US011668723B2

(12) United States Patent
Lee

(10) Patent No.: US 11,668,723 B2
(45) Date of Patent: Jun. 6, 2023

(54) AUTOMATED DISSOLUTION/PERMEATION TESTING SYSTEM

(71) Applicant: Logan Instruments Corporation, Somerset, NJ (US)

(72) Inventor: Luke Lee, Belle Mead, NJ (US)

(73) Assignee: Logan Instruments Corporation, Somerset, NJ (US)

( * ) Notice: Subject to any disclaimer, the term of this patent is extended or adjusted under 35 U.S.C. 154(b) by 384 days.

(21) Appl. No.: 16/913,560

(22) Filed: Jun. 26, 2020

(65) Prior Publication Data

US 2021/0011038 A1   Jan. 14, 2021

Related U.S. Application Data

(60) Provisional application No. 62/872,235, filed on Jul. 9, 2019.

(51) Int. Cl.
*G01N 35/00* (2006.01)
*G01N 35/08* (2006.01)

(52) U.S. Cl.
CPC . *G01N 35/00663* (2013.01); *G01N 35/00722* (2013.01); *G01N 35/08* (2013.01);
(Continued)

(58) Field of Classification Search
CPC .. G01N 35/08; G01N 33/15; G01N 35/00663; G01N 13/00; G01N 35/00; G01N 35/00722; G01N 2035/00346; G01N 2013/006; G01N 2013/003; G01N 2035/00198; G01N 2035/00891
See application file for complete search history.

(56) References Cited

U.S. PATENT DOCUMENTS

| 3,802,272 A | 4/1974 | Bischoff et al. |
| 4,158,694 A | 6/1979 | Bischoff et al. |

(Continued)

FOREIGN PATENT DOCUMENTS

WO    9716717 A1    5/1997

OTHER PUBLICATIONS

First Examination Report of Indian patent application 202014028200 dated Dec. 13, 2021.

*Primary Examiner* — Shogo Sasaki
(74) *Attorney, Agent, or Firm* — Brian Roffe

(57) ABSTRACT

Combined dissolution rate and permeation rate testing apparatus includes temperature-controllable testing cell units arranged on a housing frame. Each testing cell unit includes a donor chamber receivable of dissolution media, a receptor chamber receivable of bodily fluid, gaskets that retain a membrane between the two chambers, and controllable mixers that mix the fluid in the receptor chamber. A flow control arrangement operatively circulates dissolution media through the donor chamber and enables sampling of the dissolution media. Another flow control arrangement operatively circulates bodily fluid through the receptor chamber. An analysis unit analyzes dissolution media removed from the donor chamber and bodily fluid removed from the receptor chamber to provide data about dissolution of a pharmaceutical product dissolved in the dissolution media and permeation of the pharmaceutical product through the membrane into the bodily fluid.

20 Claims, 11 Drawing Sheets

(52) U.S. Cl.
CPC .............. *G01N 2035/00346* (2013.01); *G01N 2035/00891* (2013.01)

(56) References Cited

U.S. PATENT DOCUMENTS

| | | | |
|---|---|---|---|
| 4,335,438 A | 6/1982 | Smolen | |
| 4,450,076 A | 5/1984 | Medicus et al. | |
| 4,468,951 A | 9/1984 | Garcia et al. | |
| 4,594,884 A | 6/1986 | Bondi et al. | |
| 4,667,504 A | 5/1987 | Hobson | |
| 4,740,309 A | 4/1988 | Higuchi | |
| 4,771,004 A | 9/1988 | Higuchi | |
| 4,863,696 A * | 9/1989 | Saydek | G01N 13/00 436/178 |
| 5,030,575 A * | 7/1991 | Stofac | A01N 1/02 435/284.1 |
| 5,156,334 A | 10/1992 | Kimbell et al. | |
| 5,183,760 A * | 2/1993 | Sweetana | G01N 13/04 210/612 |
| 5,412,979 A | 5/1995 | Fassihi | |
| 5,490,415 A | 2/1996 | Mak et al. | |
| 6,022,733 A | 2/2000 | Tam et al. | |
| 6,043,027 A | 3/2000 | Selick et al. | |
| 6,294,134 B1 | 9/2001 | Schenk et al. | |
| 6,324,898 B1 | 12/2001 | Cote et al. | |
| 6,360,588 B1 | 3/2002 | Ross et al. | |
| 6,467,335 B1 * | 10/2002 | Mizobe | G01N 15/08 73/29.01 |
| 6,521,191 B1 * | 2/2003 | Schenk | G01N 13/00 422/547 |
| 7,331,251 B2 | 2/2008 | Das et al. | |
| 7,470,545 B2 | 12/2008 | Hughes | |
| 8,277,762 B2 | 10/2012 | Newsam et al. | |
| 9,464,981 B2 | 10/2016 | Gibbons et al. | |
| 9,546,991 B2 | 1/2017 | Li et al. | |
| 9,802,158 B2 | 10/2017 | Fissell et al. | |
| 10,228,358 B2 | 3/2019 | Narang et al. | |
| 2006/0127967 A1 | 6/2006 | Touitou et al. | |
| 2009/0145831 A1 | 6/2009 | Manabe et al. | |
| 2012/0167671 A1 | 7/2012 | Mikulasik et al. | |

* cited by examiner

AUTOMATED DISSOLUTION/PERMEATION TESTING SYSTEM

FIELD OF THE INVENTION

The present invention relates to automated dissolution and permeation testing systems in which for the permeation testing, the system recreates flow of release of a pharmaceutical from the stomach to the intestines using a man-made intestinal membrane. The systems of the present invention also allow for quantification of dynamic permeation of the pharmaceutical through the intestinal wall via UV or HPLC systems.

The present invention also relates to a method for performing both dissolution testing of a pharmaceutical product and permeation testing of the permeation of the pharmaceutical product through a membrane.

BACKGROUND OF THE INVENTION

Currently, the pharmaceutical industry generally only performs dissolution testing with dissolution systems; permeation testing is often considered a high aspiration goal yet is often needed in some situations.

For example, in order to do in-vitro in-vivo correlation (IVIVC), the pharmaceutical scientists require drug dissolution data and drug permeation data. Currently, there is no known system to provide the data of both in one common system or by means of a single apparatus. An in-vitro in-vivo correlation is defined by the U.S. Food and Drug Administration (FDA) as "a predictive mathematical model describing the relationship between an in-vitro property of a dosage form and an in-vivo response". Generally, the in-vitro property is the rate or extent of drug dissolution or release while the in-vivo response is the plasma drug concentration or amount of drug absorbed. The United States Pharmacopoeia (USP) defines IVIVC as "the establishment of a relationship between a biological property, or a parameter derived from a biological property produced from a dosage form, and a physicochemical property of the same dosage form".

Currently, drug permeation testing is done by many kinds of glass bottles in combination with intestinal membrane or other artificial membranes. The results of permeation testing using current equipment have had too many variables in these situations which adversely affect the permeation information about the pharmaceutical product.

Some drug permeation tests have been done using animals, continuously taking blood from the live animals. Such animal studies are simply not humane and an alternative should be implemented.

Therefore, while permeation tests of pharmaceutical products are necessary to predict the bioequivalence, there is not really any reliable instrument to perform them in combination with dissolution testing of the pharmaceutical product.

U.S. patents related to permeation testing include U.S. Pat. No. 6,043,027 (Selick et al.) which describes testing devices, systems, and methods for evaluating the permeation of various chemicals through different types of cells. One such device includes a base member and a top member having multiple wells aligned when the top member is secured to the base member. A membrane sheet includes at least one layer of cells grown on the sheet and is placed between the base member and the top member prior to assembly. Test samples are placed into the wells in the top member and samples are removed from the top and bottom wells at a later time and tested to determine the amount of the test sample which permeated through the cells.

Also, U.S. Pat. No. 8,277,762 (Newsam et al.) describes apparatus and methods for screening the effect of test formulations on barrier properties of a membrane, e.g., skin. The apparatus and methods enable more efficient measurements of skin permeabilization, of the permeation of molecular or particulate entities through skin, and of the absorption and adsorption by skin of ingredients in fluid formulations, together with screening of exfoliation of material from the exterior of the stratum corneum. The apparatus provide for fluid contact to the skin from both donor and receptor sides, for measurements of skin electrical response in the presence of test formulations, of permeation and permeation enhancement, for the depth profiling of test formulation constituents through the skin, of stratum corneum component disruption, and of loss of material from the stratum corneum.

U.S. Pat. No. 9,546,991 (Li et al.) describes a device for assessing drug dissolution, absorption and permeation including a chamber comprising a reservoir having a bottom, at least one side wall having an opening, and a hollow interior. An extension has at least one side wall, a single, open distal end, a single, open proximal end attached to the side wall at the opening, and a hollow interior. A permeability barrier has a least one side wall, an open distal end, and a proximal end, and holds a layer of cells, a tissue layer, or a layer of an artificial membrane. The proximal end of the permeability barrier contacts the distal end of the extension. A securing cap is reversibly attached to the permeability barrier or the extension, and the securing cap, permeability barrier, and chamber are in fluid communication.

WO 9716717 (Kuhfeld et al.) describes an automated permeability analysis system that increases the capacity, precision, accuracy and reliability of in vitro drug candidate permeability studies. The permeability analysis system establishes a working environment around which a robotic arm may maneuver to enable a computer to establish and carry out a multitude of simultaneous drug transport experiments, with minimal test operator involvement. The system thereby may be used on a relatively large scale to easily and accurately investigate mechanisms of drug transport across a variety of cell membranes and tissues that act as barriers to drug absorption.

These prior art apparatus do not provide for automated dissolution and permeation testing in which flow of release of a pharmaceutical from the stomach to the intestines is recreated using a man-made intestinal membrane, while at the same time, dissolution testing of the pharmaceutical product can be performed.

OBJECTS AND SUMMARY OF THE INVENTION

It is an object of at least one embodiment of the present invention to provide a new and improved permeation testing unit that also performs dissolution testing, or vice versa.

It is another object of at least one embodiment of the present invention to provide a combined dissolution and permeation testing apparatus and method.

It is yet another object of at least one embodiment of the present invention to provide a combined dissolution and permeation testing apparatus and method in particular for use in IVIVC.

It is still another object of at least one embodiment of the present invention to integrate a permeation testing system into a dissolution testing system to create a combined dissolution and permeation testing apparatus, i.e., a single housing or frame on which both dissolution testing and permeation testing are performed.

It is still another object of at least one embodiment of the present invention to integrate a permeation testing method into a dissolution testing method, or vice versa, to create a combined dissolution and permeation testing method conducted by a single apparatus.

In order to achieve one or more of the foregoing objects or others, a combined dissolution rate and permeation rate testing apparatus in accordance with the invention includes a housing having a frame, and temperature-controllable testing cell units arranged on the frame. Each testing cell unit includes a first, donor chamber receivable of dissolution media, first connecting means for enabling fluid flow into and out of the first chamber, a second, receptor chamber receivable of bodily fluid, second connecting means for enabling fluid flow into and out of the second chamber, retaining means for retaining a membrane between the first and second chambers, and controllable mixing means for mixing the fluid flowing into and out of the second chamber. A first flow control arrangement, e.g., a syringe pump arrangement, is coupled to the first connecting means and operatively circulates dissolution media into and out of the first chamber and enables sampling of the dissolution media. A second flow control arrangement, e.g., a syringe pump arrangement, is coupled to the second connecting means and operatively circulates bodily fluid into and out of the second chamber. An analysis unit analyzes dissolution media removed from the first chamber by the first flow control arrangement and bodily fluid removed from the second chamber by the second flow control arrangement to provide data about dissolution of a pharmaceutical product dissolved in the dissolution media and permeation of the pharmaceutical product through the membrane into the bodily fluid.

The mixing means may be configured to extend into the second chamber and mix fluid present in the second chamber, and may be a stirrer. Each testing cell units can further include a first housing part defining the first chamber and a second housing part defining the second chamber, in which case, clamping means are provided for clamping the first and second housing parts together, e.g., a clamp. A temperature control unit, e.g., a heater block, may be arranged on the frame and controls or regulates temperature of the testing cell units, either individually or independently or collectively. A mixing control unit may be arranged on the frame and controls actuation of the mixing means to mix the fluid flowing into and out of the second chamber. A water bath may be included to pre-heat the dissolution media to a user-selected temperature.

The membrane retaining means may include a first annular gasket arranged to be pressed toward the membrane from one side when the membrane is present and a second annular gasket arranged to be pressed toward the membrane from an opposite side when the membrane is present. Operatively, each testing cell unit includes a membrane. Also, each testing cell unit may include a donor cell defining the first chamber and a receptor cell defining the second chamber. Clamps may clamp each donor cell of a respective testing cell unit against the receptor cell of the respective testing cell unit.

A display and control screen may be arranged on the housing and coupled to the analysis unit. The second connecting means may include a receptor inlet/outlet component including a housing defining a flow passage therethrough for flow of the bodily fluid.

Each testing cell unit may include a receptor housing defining the second chamber. The receptor housing includes a circumferential wall having an opening leading to a channel extending to the second chamber, with the mixing means being situated in the channel. A vent plug vents air from the second chamber.

Each testing cell unit may include a donor housing defining the first chamber. The donor housing has a cylindrical portion. Also, the donor housing may have a first opening leading to a channel extending to the first chamber and a second opening leading to a channel extending to the first chamber. In this case, each testing cell unit also includes a donor inlet component connected to the first opening and a donor outlet component connected to the second opening. The first flow control arrangement is thus configured to direct dissolution media into the first chamber through the donor inlet component and out of the first chamber through the donor outlet component.

Other and further objects, advantages and features of the present invention will be understood by reference to the following specification in conjunction with the annexed drawings.

BRIEF DESCRIPTION OF THE DRAWINGS

The invention, together with further objects and advantages thereof, may best be understood by reference to the following description taken in conjunction with the accompanying drawings wherein like reference numerals identify like elements.

DETAILED DESCRIPTION OF THE INVENTION

Figure 1:
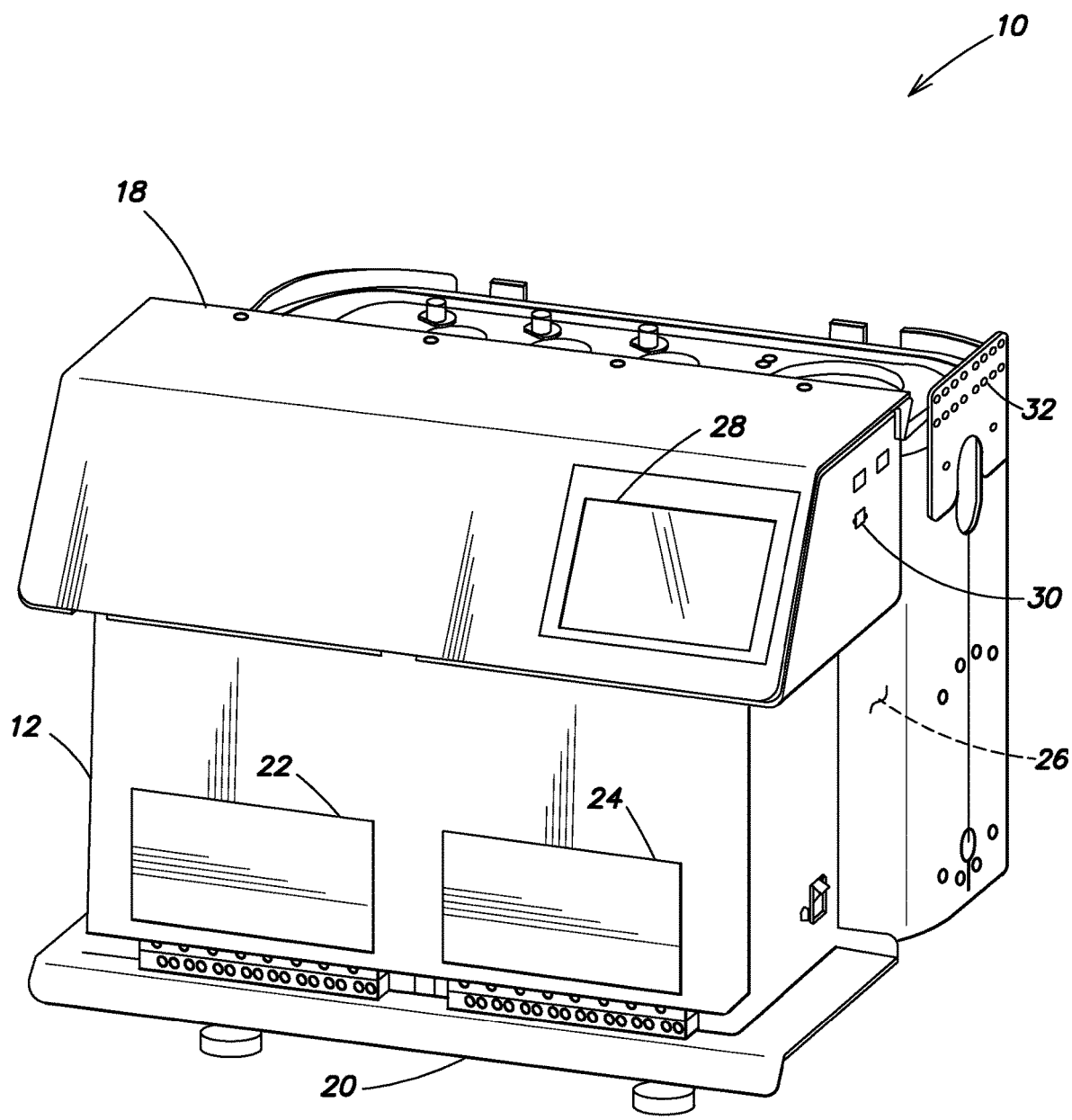
FIG. 1 is a right side perspective view of an apparatus in accordance with the invention that performs a method in accordance with the invention.
Figure 2:
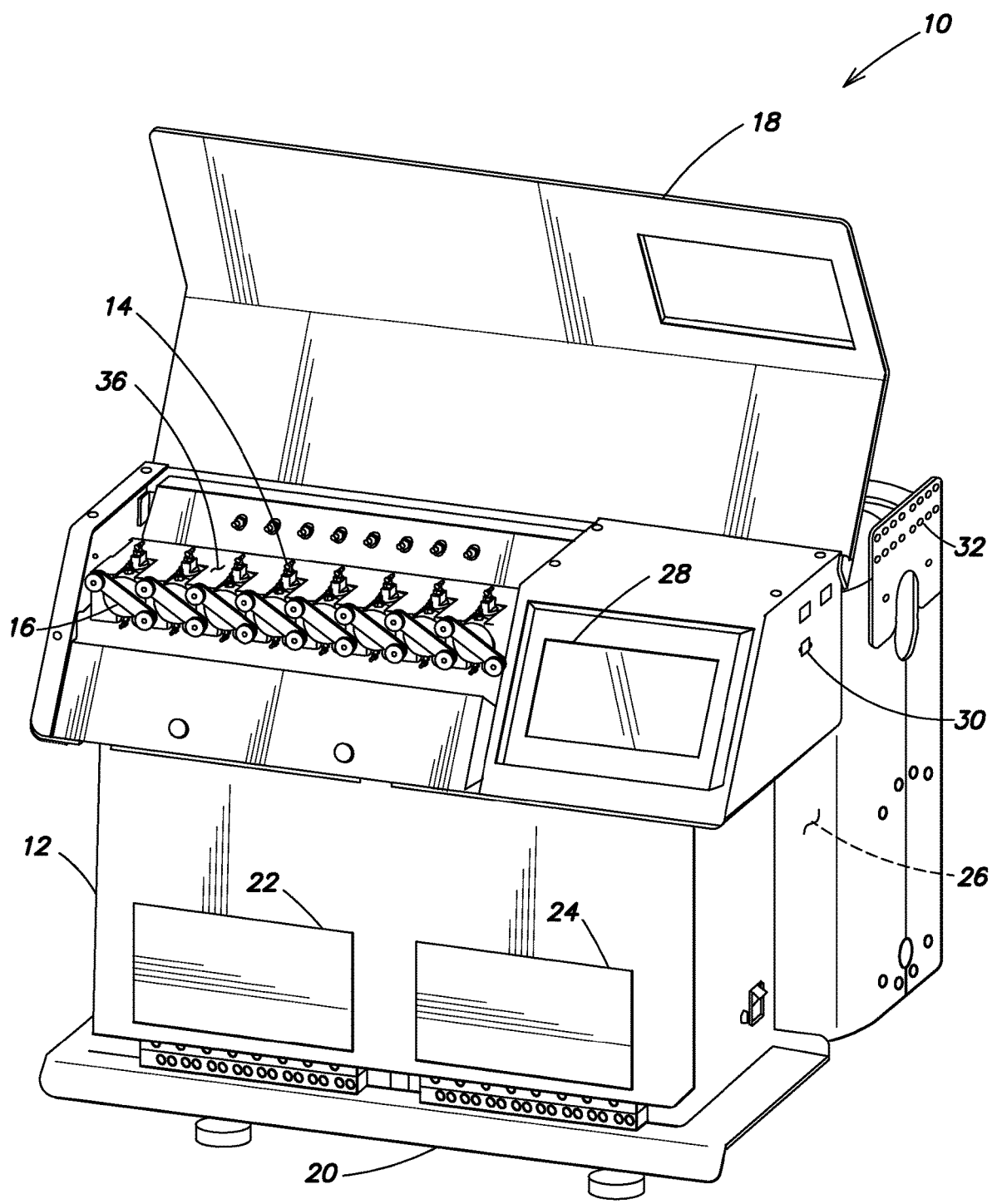
FIG. 2 is a view of the apparatus shown in FIG. 1 with the cover in an open position.
Figure 3:
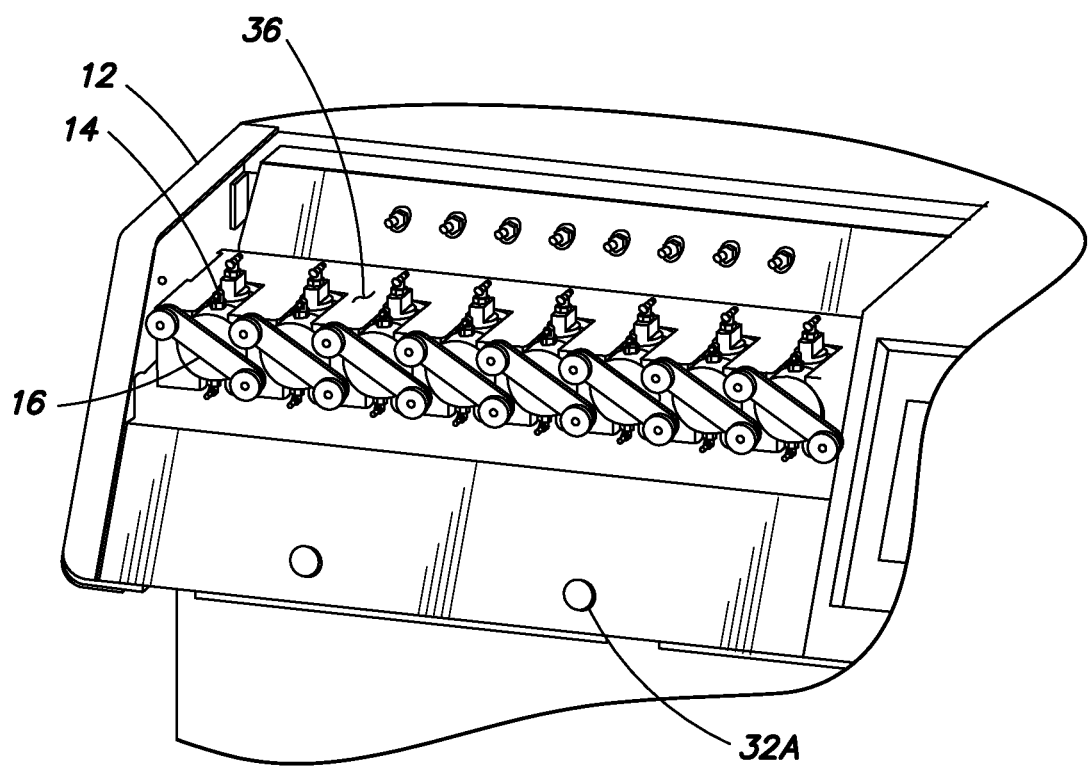
FIG. 3 is an enlarged view of the heater block of the apparatus shown in FIG. 1.

Referring to the accompanying drawings wherein like reference numerals refer to the same or similar elements, FIGS. 1-3 are perspective views of an apparatus 10 in accordance with the invention which automates permeation testing and performs such permeation testing in combination with a dissolution system that performs dissolution testing of pharmaceutical products. Herein, the apparatus 10 may be considered an automated dissolution/permeation testing system or arrangement.

Generally, the apparatus 10 includes a housing 12 including a frame, and a plurality of permeation testing cell units 14 each including a donor cell that holds dissolution media or solution which circulates or is circulated therethrough, a receptor cell that holds the bodily fluid (media), a mixing device to mix the fluid, and one or more clamps 16 to hold the permeation testing cell unit together and clamp a membrane between the donor cell and the receptor cell. The permeation testing cell units 14 are arranged in the housing 12 and/or on the frame. As shown in FIG. 1, the permeation testing cell units 14 may be situated in an enclosure formed by the housing 12, with an access portal (cover 18) connected to the frame to enable selective access to the permeation testing cell units 14 in their enclosure.

FIG. 1, and sometimes FIG. 2, also shows other structure, including a bottom board 20, a housing for a dissolution sampling pump arrangement 22, a housing for a permeation sampling pump arrangement 24, a water bath 26, a display and control (touch) screen 28, a control box 30, a tubing manifold 32 and a vessel plate 34. A heater block 36 is shown in FIG. 2 when the cover 18 is in the open state or position. The dissolution sampling pump arrangement 22 and the permeation sampling pump arrangement 24 may each comprise a syringe pump arrangement, a peristaltic pump arrangement or a ceramic pump arrangement.

All of the permeation testing cell units 14 in the apparatus 10 preferably have the same exact construction, but it is possible to use differently constructed permeation testing cell units 14 provided they have the same functionality as those disclosed herein. The permeation testing cell units 14 are also configured to be temperature-controlled or temperature-controllable.

The membrane represents, for example, an intestinal wall. That is, the membrane may be any type of membrane that has properties which are the same as or similar to an intestinal wall or other body part for which permeation testing is undertaken. Preferably, the membrane is PERMEFILM™, a product developed by the current assignee/applicant, Logan Instruments Corp.

The mixing device may be any type of mixing device used to mix fluid, such as a stirrer. The mixing device may be operative on the fluid in the receptor cell by extending into a chamber in the receptor cell.

Depending on the construction of the cell unit, only one clamp 16 may be required to hold the cell unit components together or multiple clamps may be needed to hold the cell unit components together.

The apparatus 10 also includes a temperature control unit in control box 30 that individually, independently or collectively controls the temperature of the permeation testing cell units 14 such that these may be referred to as temperature-controllable testing units (but hereinafter generally referred to as permeation testing cell units or testing cell units), see FIGS. 1 and 2. The temperature control unit is arranged in the housing 12 and/or on the frame. Often, the temperature control unit is in the form of a heater to receive and heat all of the permeation testing cell units 14 when received. The temperature control unit may be of a type which is set by a user and optionally has a feedback control to ensure that the permeation testing cell units 14 are at the desired temperature. Construction and use of such a temperature control unit are within the skill level of those possessing knowledge of pharmaceutical testing apparatus.

A mixing control unit may also be arranged in or part of control box 30, and thus is at least partly in the housing 12 and/or on the frame, see FIGS. 1 and 2, and is coupled to the mixing devices in order to drive the mixing devices in a controlled manner. If the mixing devices are stirrers, the mixing control unit would be configured to drive the stirrers in the permeation testing cell units 14, e.g., it would function as a cell driver system.

The dissolution sampling pump arrangement 22 circulates dissolution solution or media through the permeation testing cell units 14 and/or samples the dissolution media flowing through the donor side of the permeation testing cell units 14, and the permeation sampling pump arrangement 24 handles the intestinal fluid or other bodily fluid being provided to the receptor side of the permeation testing cell units 14. The sampling pump arrangements 22, 24 are arranged in the housing 12 and/or on the frame.

Sampling pump arrangements 22, 24 may be conventional systems of a type considered as flow control arrangements. Each sampling pump arrangement 22, 24 comprises a plurality of similar pump devices and associated conduits that enable independent flow of fluid to and from a respective permeation testing cell unit 14.

The couplings and flow conduits between the interior space of vessels used for dissolution testing and the dissolution sampling pump arrangement 22 and the permeation testing cell units 14, and between the dissolution sampling pump arrangement 22 and the dissolution rate analysis system (e.g., arranged in housing 12) are situated in or on the apparatus 10, and described below with reference to FIGS. 7, 9 and 11. The manner of control of the dissolution sampling pump arrangement 22, and the positioning and use of the couplings and flow conduits, whether part of tubing manifold 32 or otherwise, to effect such fluid transfer is within the capability of those skilled in the art to which this invention pertains.

The couplings and flow conduits between the intestinal or other bodily fluid reservoir or source used for permeation testing and the permeation sampling pump arrangement 24 and the permeation testing cell units 14, and between the permeation sampling pump arrangement 24 and the permeation rate analysis system (e.g., arranged in housing 12), are situated in or on the apparatus 10, and described below with reference to FIGS. 9-11. The manner of control of the permeation sampling pump arrangement 24, and the positioning and use of the couplings and flow conduits, to effect such fluid transfer is within the capability of those skilled in the art to which this invention pertains.

The water bath 26 pre-heats the dissolution media to a user-selected temperature, see FIGS. 1 and 2. The water bath 26 is arranged in the housing 12 and/or on the frame. Structure similar to a water bath may be used in the apparatus as in accordance with the invention. Such structure may be integral with the housing 12 and/or frame or separate therefrom and fluidly connected to the dissolution sampling pump arrangement 22.

An overall design consideration for the permeation testing cell unit 14 is to have the dissolution solution or media (which interacts with the pharmaceutical being tested) circulating in the donor cell, while on the other side of the donor cell, the receptor holds the bodily fluid (PBS pH.74). An artificial intestinal membrane (PERMEFILM™ or otherwise) is clamped or otherwise secured between the donor and receptor cells in contact with the dissolution solution or media in the donor cell and the bodily fluid in the receptor cell, while the mixing device or stirrer in the receptor cell agitates the bodily fluid. Agitation of the bodily fluid simulates absorption of the pharmaceutical, dissolved into the dissolution solution or media, into the bodily fluid. It then becomes possible to analyze the bodily fluid sample from the receptor cell to determine how much of the pharmaceutical is being released and permeating through the membrane.

As seen in FIGS. 2 and 3, the temperature control unit comprises the heater block 36 arranged to define cavities for retaining the permeation testing cell units 14. The mixing control unit comprises a cell drive or driver system arranged in connection with the permeation testing cell units 14. The dissolution sampling pump arrangement 22 is at a lower portion of the apparatus 10 on one side while the permeation sampling pump arrangement 24 is on the other side of the apparatus 10. The water bath 26 may be behind the heater block 36, cell drive system and sampling pump arrangements 22, 24. A portion 32A of the tubing manifold 32 is also visible when the cover 18 is lifted upward.

Figure 4:
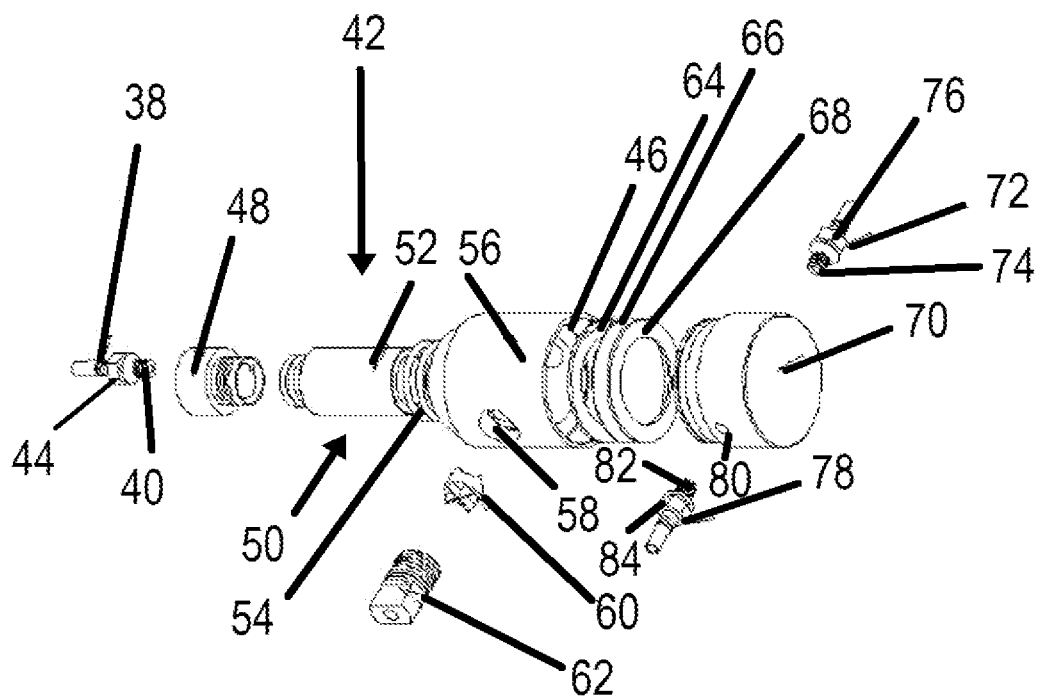
FIG. 4 is an exploded view of a permeation testing cell unit used in the apparatus in accordance with the invention.

Apparatus 10 also includes the display and control screen 28 on the front of the housing 12, see FIGS. 1 and 2, and the control box 30 includes an analysis unit or electronics inside the housing 12. The electronics are connected to the various components and enable control of the components via user-entry on the display and control screen 28 or any other type of user interface whether wired to the electronics or communicating with the electronics wirelessly. The electronics may include a control unit, a processor, a communications unit, a data processing unit, a data storage unit, other necessary hardware components and components which retain software, and enable performance of the testing provided by apparatus 10. The display and control screen 28 can also provide results of the testing, and can be configured to provide a color or black and white display. The electronics may be easily configured by persons having skill in the art of dissolution data processing to render results as well as permeation data processing to derive permeation data about the pharmaceutical product/membrane arrangement FIG. 4 is an exploded view of a preferred construction of the permeation testing cell unit 14 in accordance with the invention. This permeation testing cell unit 14 is also considered an invention herein. Permeation testing cell unit 14 preferably has the shape and form as shown in FIG. 3 but is not limited to this form and/or shape and may have alternative forms and shapes.

Permeation testing cell unit 14 includes as for the receptor cell, an elongate receptor inlet/outlet component 38 at one end through which bodily fluid operationally flows. Receptor inlet/outlet component 38 includes a housing defining a flow passage therethrough for flow of the bodily fluid. The flow passage has an opening at the first end (at the left in FIG. 4) and an opening at the opposite end (at the right in FIG. 4). Receptor inlet/outlet component 38 also includes connecting means 40 for connecting the receptor inlet/outlet component 38 to one end of a generally elongate receptor housing 42. These connecting means 40 may comprise a thread formed at the outlet end of the receptor inlet/outlet component 38. Receptor housing 42 is also part of the receptor cell.

A bolt 44 is arranged on the receptor inlet/outlet component 38 or formed integral therewith to enable tightening of the receptor inlet/outlet component 38 in connection with the receptor housing 42 or release of the receptor inlet/outlet component 38 from engagement with the receptor housing 42. Bolt 44 is not an essential part of the receptor inlet/outlet component 38 and other structure that enables tightening of the receptor inlet/outlet component 38 to the receptor housing 42 may be used in the invention.

The receptor housing 42 defines a chamber 46 therein in flow communication with flow passage of the receptor inlet/outlet component 38 when the receptor inlet/outlet component 38 is engaged with the receptor housing 42. Receptor housing 42 includes a first receptor housing part 48 which defines a receptacle to receive the threaded end of the receptor inlet/outlet component 38 and a second receptor housing part 50 connected to the first receptor housing part 48. The connection may be a releasable (temporary) connection or a permanent connection. That is, the first and second receptor housing parts 48, 50 may be formed integral with one another or as separate parts and connected thereto.

The first receptor housing part 48 includes a flow passage in flow communication with flow passage of the receptor inlet/outlet component 38 when the receptor inlet/outlet component 38 is engaged with the receptor housing 42, while the second receptor housing part 50 includes the chamber 46 in flow communication with the flow passage of the first receptor housing part 48. As such, bodily fluid on the receptor side can flow through receptor inlet/outlet component 38 to the first receptor housing part 48 and then to the second receptor housing part 50.

When the first and second receptor housing parts 48, 50 are formed to be removable from one another, connecting structure is provided on the first and second housing parts 48, 50 to enable them to be releasably connected together, e.g., cooperating threads with one thread being on an outer surface of a projection on the first receptor housing part 48 and the other complementary thread being on an inner surface of a projection on the second receptor housing part 50. This connecting structure may be any connection means for connecting two housing parts together.

Second receptor housing part 50 may have an elongate cylindrical section 52 with a first diameter and then an angled or sloping section 54 leading to another elongate cylindrical section 56 with a larger diameter. The second receptor housing part 50 is dimensioned to define the chamber 46 having an appropriate size for permeation testing. The bodily fluid remains in this chamber 46 for about two hours and provides a measure of permeation of the dissolution solution or media through the membrane retained between the donor and receptor sides.

Housing section 56 is provided with an opening 58 in a circumferential wall leading to the chamber 46 in the second receptor housing part 50. Opening 58 provides a conduit between the chamber 46 and the exterior of the second receptor housing part 50. A mixing device 60, such as a stirrer, is configured to fit into the opening 58. Mixing device 60 is designed to partly extend into the chamber 46 in order to mix or agitate any fluid in the chamber 46. The relative size of the mixing device 60 and chamber 46 can be adjusted to ensure the mixing device 60 is able to perform its intended mixing functionality. Mixing device 60 is referred to herein as mixing means for mixing the bodily fluid in the chamber 46.

A vent plug 62 engages with the opening to secure the mixing device 60 in the opening 58. Vent plug 62 may include threads on an outer surface that engage with threads on a surface defining the opening 58. Other means for securing the vent plug 62 in connection with the second receptor housing part 50 are also envisioned within the scope and spirit of the invention. Mixing device 60 and vent plug 62 are also part of the receptor cell.

Vent plug 62 is configured to allow for release of air from the chamber 46. Bodily fluid is inserted into chamber 46 through the receptor inlet/outlet connector 38 and any air present can be vented via the vent plug 62.

A first gasket 64 is positioned at an open end of the second receptor part 50 adjacent the chamber 46. A membrane 66 used for permeation testing is placed against this gasket 64 while a second gasket 68 is placed on the other side of the membrane 66. Each gasket 64, 68 is annular and the membrane 66 is sandwiched between the gaskets 64, 68. As mentioned previously, the membrane 66 is preferably one marketed by the current assignee under the tradename PERMEFILM™. The membrane 66 may be in contact around its circumferential edges with both gaskets 64, 68.

One surface of the membrane 66 is in substantial contact with the bodily fluid in the chamber 46 in the receptor housing 42. The bodily fluid does not leak out in view of the presence of the gasket 64 pressing against the membrane 66. Alternative or additional sealing structure may be provided.

The donor side or donor cell of the permeation testing cell unit 14 includes a donor housing part 70 which is substantially cylindrical and includes a chamber therein. An inlet opening is formed in a circumferential wall and a donor inlet component 72 is connected to the donor housing part 70 via this opening. Donor inlet component 72 defines a flow passage for dissolution solution that has an inlet end (at the right in FIG. 4) and an outlet end (at the left in FIG. 4). Donor inlet component 72 also includes connecting means 74 for connecting the donor inlet component 72 to the opening in the donor housing part 70. These connecting means 74 may comprise a thread formed at the outlet end of the donor inlet component 72. Donor inlet component 72 is also part of the donor cell.

A bolt 76 is arranged on the donor inlet component 72 or formed integral therewith to enable tightening of the donor inlet component 72 in connection with the donor housing part 70 or release of the donor inlet component 72 from engagement with the donor housing part 70. Bolt 76 is not an essential part of the donor inlet component 72.

The donor cell also includes a donor outlet component 78. To engage the donor outlet component 78 with the donor housing part 70, an outlet opening 80 is formed in the circumferential wall of the donor housing part 70 and the donor outlet component 78 is connected to the donor housing part 70 via this outlet opening 80. Donor outlet component 78 defines a flow passage for dissolution solution that has an inlet end (at the right in FIG. 4) and an outlet end (at the left in FIG. 4). Donor outlet component 78 also includes connecting means 82 for connecting the donor outlet component 78 to the outlet opening 80 in the donor housing part 70. These connecting means 82 may comprise a thread formed at the inlet end of the donor outlet component 78.

A bolt 84 is arranged on the donor outlet component 78 or formed integral therewith to enable tightening of the donor outlet component 78 in connection with the donor housing part 70 or release of the donor outlet component 78 from engagement with the donor housing part 70. Bolt 84 is not an essential part of the donor outlet component 78.

On the donor side, dissolution solution (or media which contains a dissolving pharmaceutical product such as a tablet or dosage form) flows through the donor inlet component 72, into a chamber in the donor housing part 70 and then out of this chamber through the donor outlet component 78.

One surface of the membrane 66 is in substantial contact with the dissolution solution in the chamber in the donor housing part 70 as the dissolution solution flows through this chamber. The dissolution solution does not leak out in view of the presence of the gasket 68 pressing against the membrane 66. Alternative or additional sealing structure may be provided.

Gaskets 64, 68 may be considered as retaining means for retaining a membrane while enabling a portion of the membrane on each side to be exposed to the fluid in a respective one of the two chambers, i.e., either chamber 46 on the receptor side through which bodily fluid operatively flows or the chamber on the donor side through which dissolution solution operatively flows. Membrane 66 allows for fluid flow therethrough depending on its properties and characteristics. Gasket 64 is operatively pressed against one side of the membrane 66 possibly being in direct contact with the membrane 66, while gasket 68 is operatively pressed against the opposite side of the membrane 66, also possibly being in direct contact with the membrane 66. As a result of this operatively pressing from opposite directions, the membrane 66 is securely retained in the permeation testing cell unit 14. Other membrane retaining means may be used in the invention and would be apparent to those skilled in the art to which this invention pertains in view of the disclosure herein. These other membrane retaining means may also include two components or members on opposite sides of the membrane 66 which cooperate to create a pressing effect to secure the membrane 66 in place.

Permeation testing cell unit 14 thereby provides for inflow and outflow of dissolution solution through the donor cell against one side of the membrane 66 and inflow of bodily fluid into a chamber 46 against the other side of the membrane 66 and mixing of the bodily fluid in this chamber 46. Outflow of the bodily fluid after a certain amount of time sufficient to enable the permeation testing (e.g., two hours) is also effected through the receptor inlet/outlet connector 38. Sealing structure is provided to reduce and ideally prevent leakage of both bodily fluid from the receptor side of the permeation testing cell unit 14 and dissolution solution from the donor side. The gaskets 64, 68 are representative of part of such sealing structure and other sealing structure with or without gaskets 64, 68 may be used as known to those skilled in the art to which this invention pertains.

Figure 5:
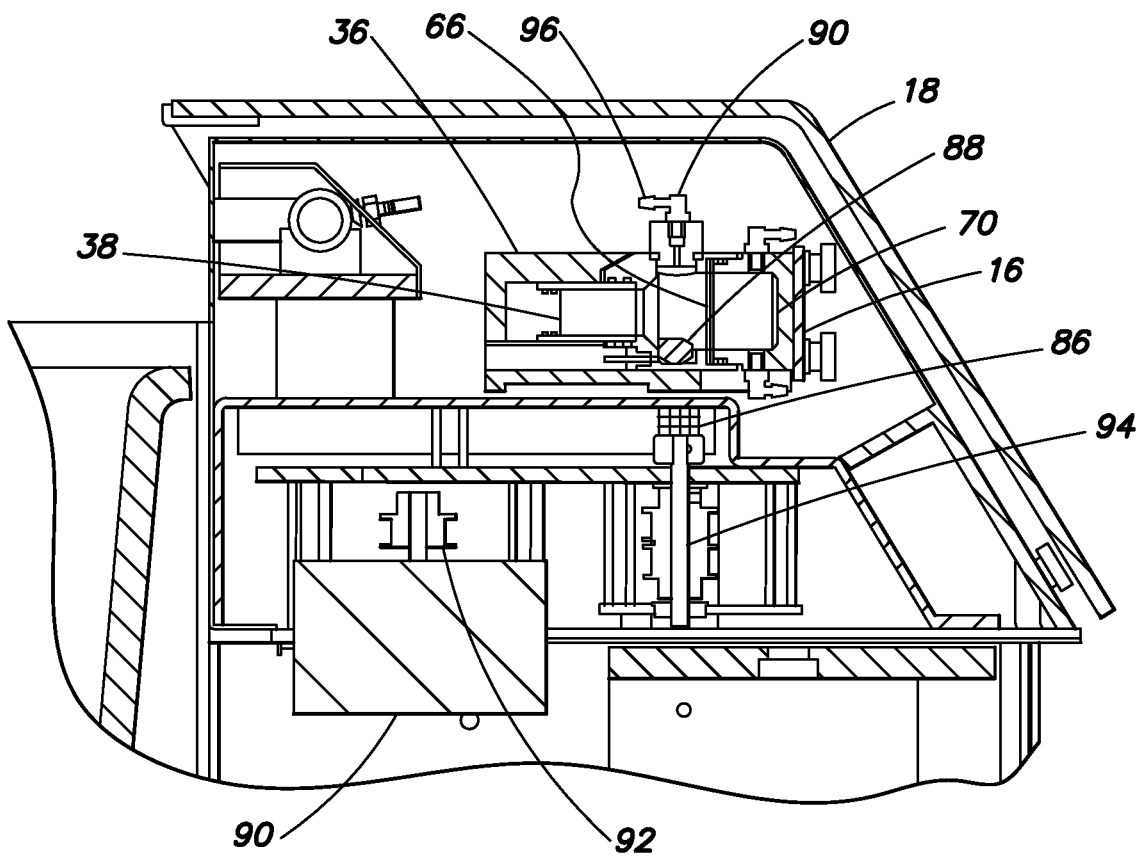
FIG. 5 is a cross-sectional view of the apparatus shown in FIG. 1.

As best seen in FIG. 5, clamps 16, or other comparable clamping means, are provided to press the donor cell against the membrane 66 in a direction toward the receptor cell while causing pressing of the receptor cell against the membrane 66 in a direction toward the donor cell. There is one clamp 16 for each permeation testing cell unit 14. This clamping is important for leakage prevention, in combination with gaskets 64, 68.

More specifically, the clamps 16 are mounted at each one end to the heater block 36 and can pivot between a position securing the donor housing part 70 in the heater block 36 and position in which removal or insertion of the permeation testing cell unit 14 into a cavity in the heater block 36 is possible. There are conduits leading to the donor inlet components 72 and conduits leading to the donor outlet components 78. FIG. 5 also shows additional structure including particulars of the mixing device 60, namely, a magnet stirrer 86, a magnet stir bar 88, an electric motor 90, a pulley 92, a pulley shaft 94 and a luer connector 96. Mixing device 60 may be constructed differently, and the invention is not limited to any particular mixing device.

Figure 6:
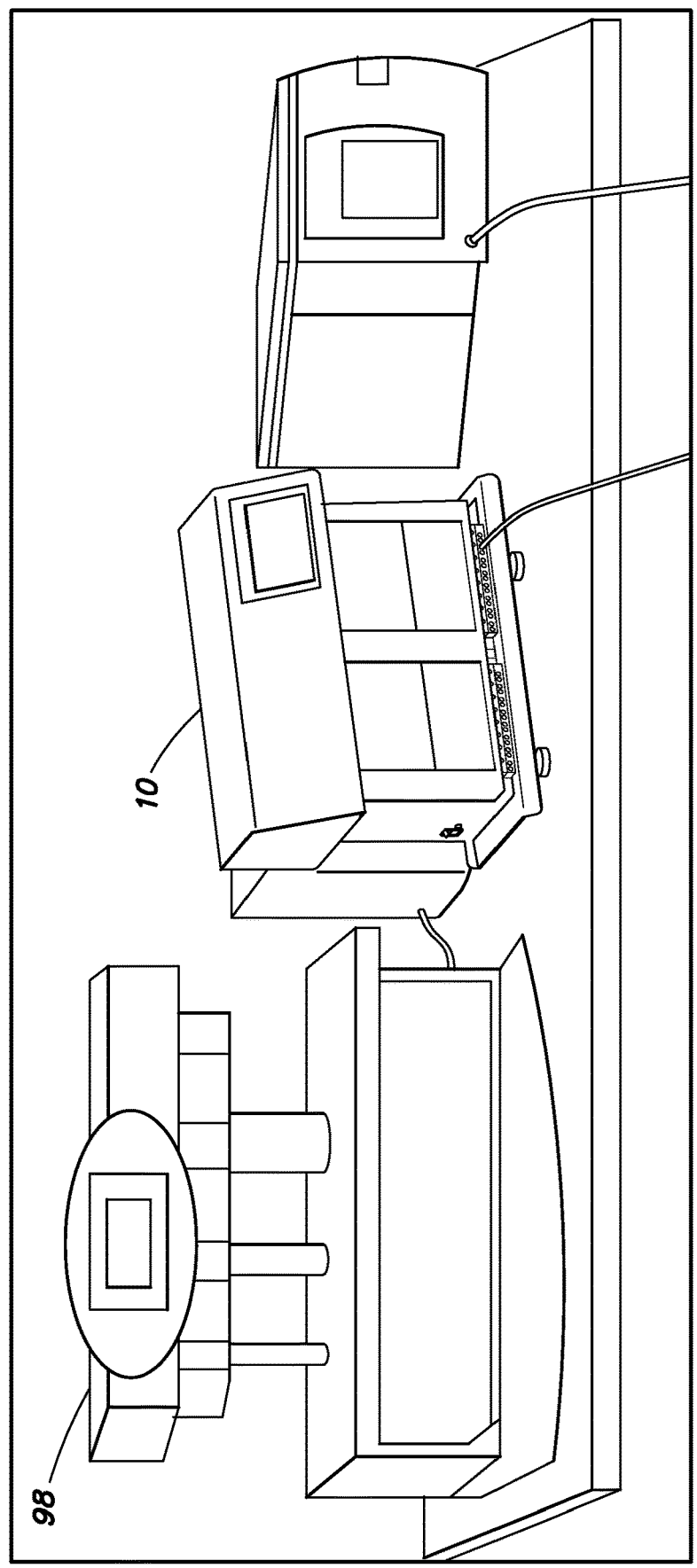
FIG. 6 is a schematic showing the apparatus of FIG. 1 with an 8-position USP apparatus 1 and 2 dissolution tester.

FIG. 6 is a schematic of an arrangement in which the apparatus 10 is used with 8-position USP apparatus 1 and 2 dissolution testers (designated 98 of a type manufactured by Logan Instruments Corporation). An exemplifying schematic of this use of apparatus 10 is shown in FIG. 7. To operate with 8-positions USP apparatus 1 and 2 dissolution testers 98, an exemplifying method is as follows:

1. Pharmaceutical tablets, as an example of a pharmaceutical product for which permeation and dissolution information is sought, are placed into vessels in the USP apparatus 98 and then syringe or other pumps of dissolution sampling pump arrangement 22 of apparatus 10 are actuated to transfer the dissolution samples thus-created into the donor cells of the permeation testing cell units 14 while the tablets are dissolving. Flow couplings are made as necessary, e.g., between the vessels and the syringe pumps of the dissolution sampling pump arrangement 22 of apparatus 10.

2. The dissolution sample in each donor cell slowly penetrates the membrane 66 of the respective permeation testing cell unit 14 (representing for example an intestinal wall) and then is transferred into the media in the chamber 46 of the receptor cells (the intestinal fluid or other bodily fluid).

3. Syringe or other pumps from permeation sampling pump arrangement 24 are actuated to take the pre-heated media from the respective vessel contained in the water bath 26. This actuation may occur simultaneous with or after the actuation of the syringe or other pumps of dissolution sampling pump arrangement 22.

4. Syringe or other pumps from dissolution sampling pump arrangement 22 are continually transferring the dissolution samples into the donor cells through donor inlet component 72 and donor outlet component 78 which are looped with the dissolution sampling pump arrangement 22 and the interior of the vessels.

5. Permeation sampling pump arrangement 24 is actuated periodically to take permeation samples and collect them into tubes retained on the apparatus or elsewhere. It is often desired to wait a set period of time until media from chamber 46 is removed from the receptor housing 42, e.g., two hours. Thus, a timing mechanism is provided to time the process and refrain from removing bodily fluid from the chamber 46 through the receptor inlet/outlet connector 38 until the set period of time has elapsed.

Indeed, this process takes hours and up to twenty permeation sets, samples can be taken. It is then possible to analyze the samples and obtain the permeation rate. In combination with dissolution testing, apparatus 10 therefore simplifies and automates the process by means of which samples of bodily fluid into which pharmaceutical products have been transferred after passing through the membrane 66 are obtained and prepared for analysis to determine permeation rate of the pharmaceutical product into the bodily fluid.

Figure 7:
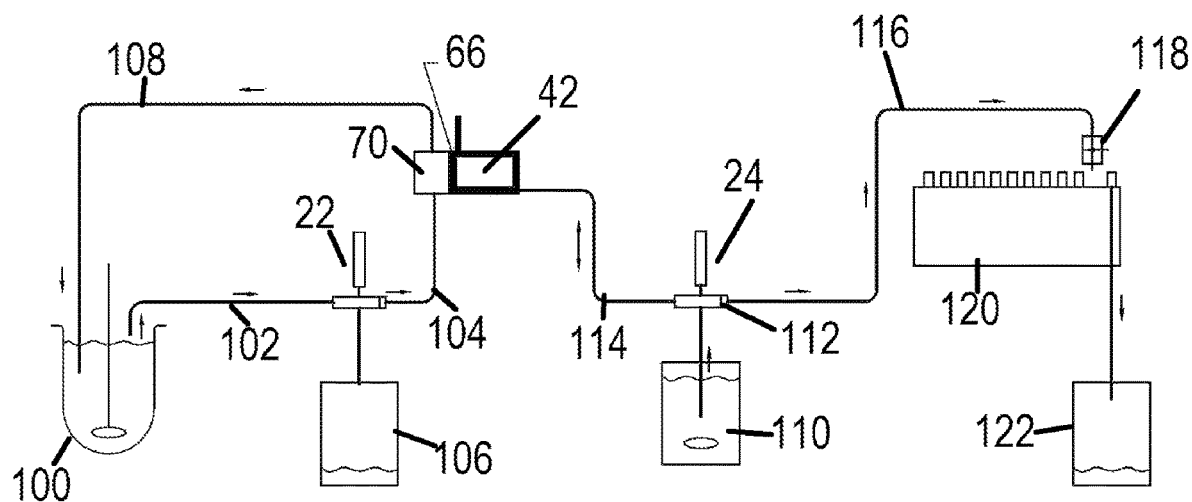
FIG. 7 is a flow schematic of one manner of use of the arrangement of FIG. 6.

FIG. 7 is a schematic of the one manner in which permeation testing can be achieved using the arrangement in accordance with the invention (described above with respect to FIG. 6). Note that the apparatus may be used for permeation testing alone without requiring dissolution testing, although it is a possibility and is performed in a preferred method. Also, the description is for a single vessel but there may be multiple vessels and respective systems for processing the media in those vessels, or multiple vessels and single system for processing the media in a plurality of those vessels.

On the donor side of the permeation testing cell unit 14, the left side of the membrane 66, the fluid flow is from a respective vessel 100 in which, for example, the pharmaceutical tablet is dissolved, through a conduit system 102 and through a respective flow valve 104 of the permeation sampling pump arrangement 24 and media replacement container 106, to the chamber in the donor housing part 70 of the respective permeation testing cell unit 14. Through a conduit system 108, the dissolution media is withdrawn from the chamber in the donor housing part 70 back to the vessel 100. On the receptor side of the permeation testing cell unit 14, there is a source of bodily fluid 110 associated with the permeation sampling pump arrangement 24 and flow valve(s) 112 thereof, which controls the flow of the bodily fluid to and from the respective chamber 46 in the receptor housing 42 (to the right of the membrane 66 in FIG. 7) through a conduit system 114. The permeation sampling pump arrangement 24 and flow valve(s) 112 thereof also direct, when desired or according to a program, bodily fluid from the chambers 46 through a conduit system 116 to a moving head 118 associated with the sample collector 120 to thereby deposit the bodily fluid in a plurality of sample-receiving vessels and enable the permeation testing and dissolution testing. A waste collector 122 receives the analyzed bodily fluid samples from the sample collector 120. Each conduit system may include one or more conduits and associated flow structure to provide for secure flow of the fluid between the connected components.

Figure 8:
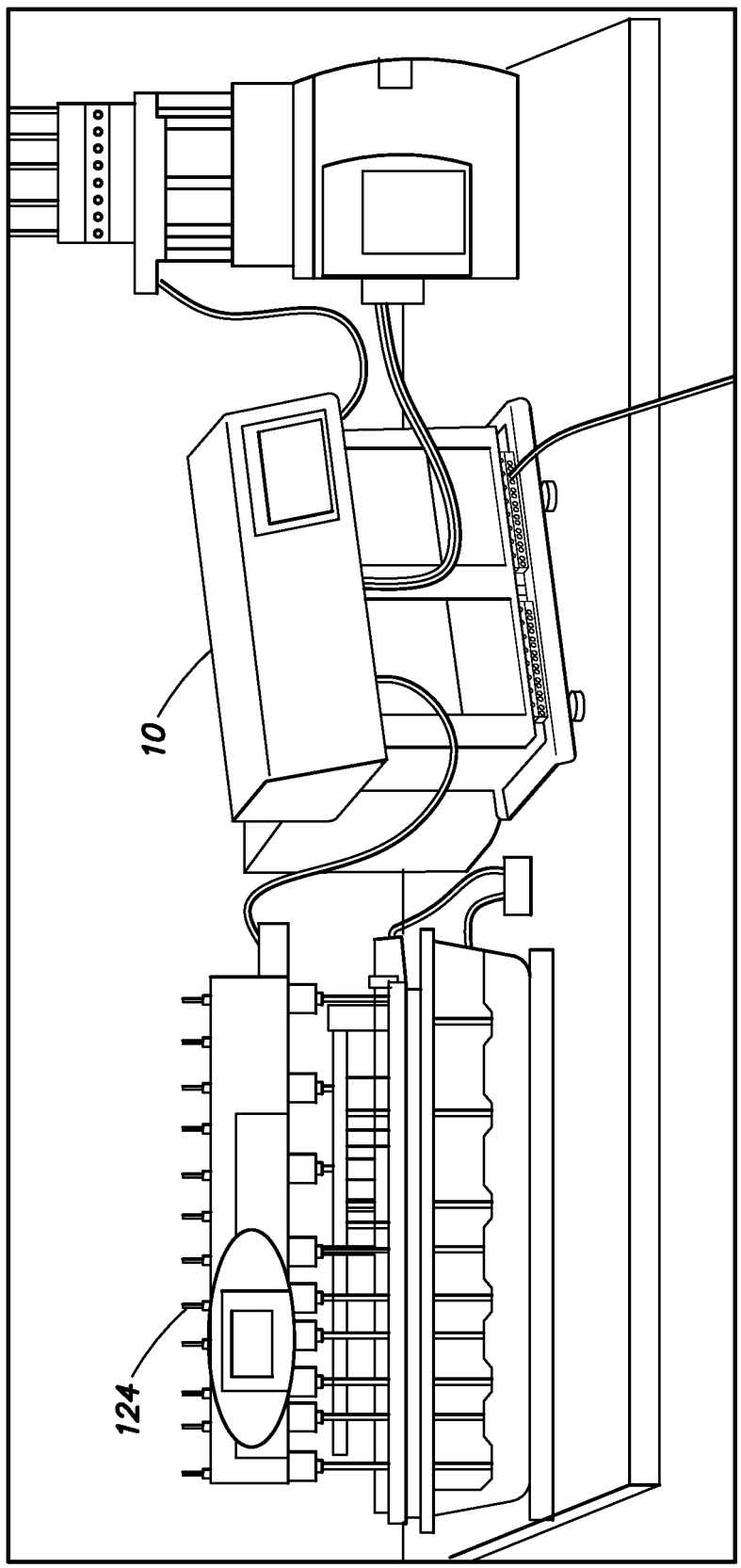
FIG. 8 is a schematic showing the apparatus of FIG. 1 with a 12-position USP apparatus 1 and 2 dissolution tester.

FIG. 8 is an arrangement in which the apparatus 10 is used with 12-position USP apparatus 1 and 2 dissolution testers (designated 124 of a type manufactured by Logan Instruments Corporation). An exemplifying schematic of this use of apparatus 10 is shown in FIG. 9. To operate with 12-positions USP apparatus 1 and 2 dissolution testers 124, an exemplifying method is as follows:

1. Twelve pharmaceutical tablets, as an example of a pharmaceutical product for which permeation and dissolution information is sought, are placed into vessels in the USP apparatus 124. Of these twelve tablets, six tablets are for dissolution and six tablets are for permeation studies, and each set of six is preferably placed in a common row.

2. Syringe or other pumps from dissolution sampling pump arrangement 22 of apparatus 10 are actuated to transfer the six dissolution samples thus-created into glass tubes or other vessels while the tablets are dissolving. Flow couplings are made as necessary, e.g., between the glass tubes and the syringe or other pumps of the dissolution sampling pump arrangement 22 of apparatus 10. These glass tubes may be retained on the apparatus 10 or elsewhere.

3. In the other six channels, a peristaltic pump or similar device transfers the dissolution samples from the other six vessels to donor cells while the tablets are dissolving.

4. Over time, the dissolution sample in each donor cell slowly penetrates the membrane 66 of the respective permeation testing cell unit 14 (representing for example an intestinal wall) and then is transferred into the media in the chamber 46 of the receptor cells (the intestinal fluid or other bodily fluid).

5. Syringe or other pumps of permeation sampling pump arrangement 24 are actuated to take the pre-heated media from the respective vessel contained in the water bath 26. This actuation may occur simultaneous with or after the actuation of the syringe or other pumps of dissolution sampling pump arrangement 22.

6. Syringe or other pumps of dissolution sampling pump arrangement 22 are continually transferring the dissolution samples from the six channels into the donor cells through donor inlet component 72 and donor outlet component 78 which are looped with the dissolution sampling pump arrangement 22 and the interior of the vessels.

7. Permeation sampling pump arrangement 24 is actuated periodically to take permeation samples and collect them into tubes, retained by the apparatus or elsewhere. It is often desired to wait a set period of time until media from chamber 46 is removed from the receptor housing 42, e.g., two hours. Thus, a timing mechanism is provided to time the process and refrain from removing bodily fluid from the chamber 46 through the receptor inlet/outlet connector 38 until the set period of time has elapsed.

Often, this process takes hours and up to twenty permeation sets, samples can be taken. It is then possible to analyze the samples and obtain the permeation rate. In combination with dissolution testing, apparatus 10 therefore simplifies and automates the process by means of which samples of bodily fluid into which pharmaceutical products have been transferred after passing through the membrane 66 are obtained and prepared for analysis to determine permeation rate of the pharmaceutical product into the bodily fluid.

Figure 9:
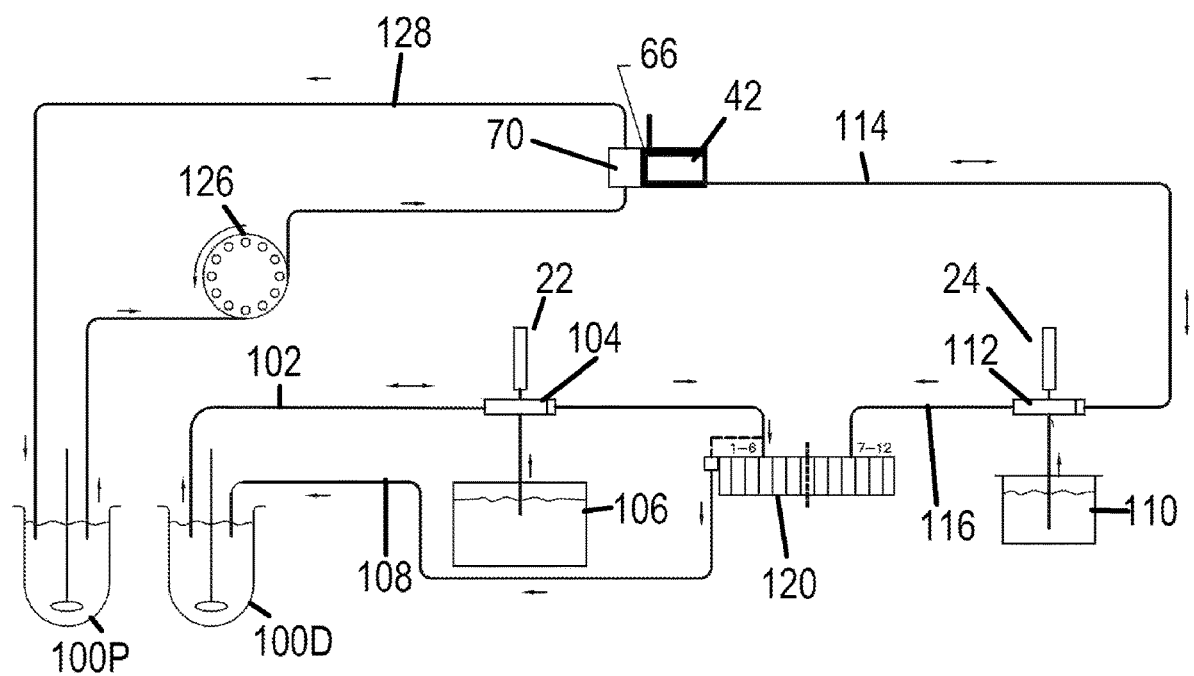
FIG. 9 is a flow schematic of one manner of use of the arrangement of FIG. 8.

FIG. 9 is a schematic of the one manner in which permeation testing can be achieved using the arrangement in accordance with the invention (described above with respect to FIG. 8). The flow valves 104 of dissolution sampling pump arrangement 22 transfer dissolution samples from six vessels designated dissolution vessels 100D while the pharmaceutical tablets are dissolving using conduit system 102 and direct samples to the sample collector 120. Through the conduit system 108, the dissolution media is withdrawn from the chamber in the respective donor housing part 70 back to the vessel 100. One or more peristaltic pumps 126 or similar device transfers the dissolution samples from the other six vessels designated permeation vessels 100P to the donor side of the permeation testing cell units 14 while the tablets are dissolving via a conduit system 128 including portions before and after the permeation testing cell units 14 in the flow direction. On the receptor side of the permeation testing cell unit 14, the permeation sampling pump arrangement 24 and its flow valve(s) 112 control the flow of the bodily fluid from the source of bodily fluid 110 and to and from the chambers 46 of the receptor housings 42 (to the right of the membrane 66 in FIG. 9) through the conduit system 114. The permeation sampling pump arrangement 24 and flow valve(s) 112 thereof also direct, when desired or according to a program, bodily fluid from the chambers 46 through the conduit system 116 to the sample collector 120 to thereby deposit the bodily fluid in a plurality of sample-receiving vessels. As such, samples for both permeation testing and dissolution testing are obtained by the sample collector 120. Each conduit system may include one or more conduits and associated flow structure to provide for secure flow of the fluid between the connected components.

Figure 10:
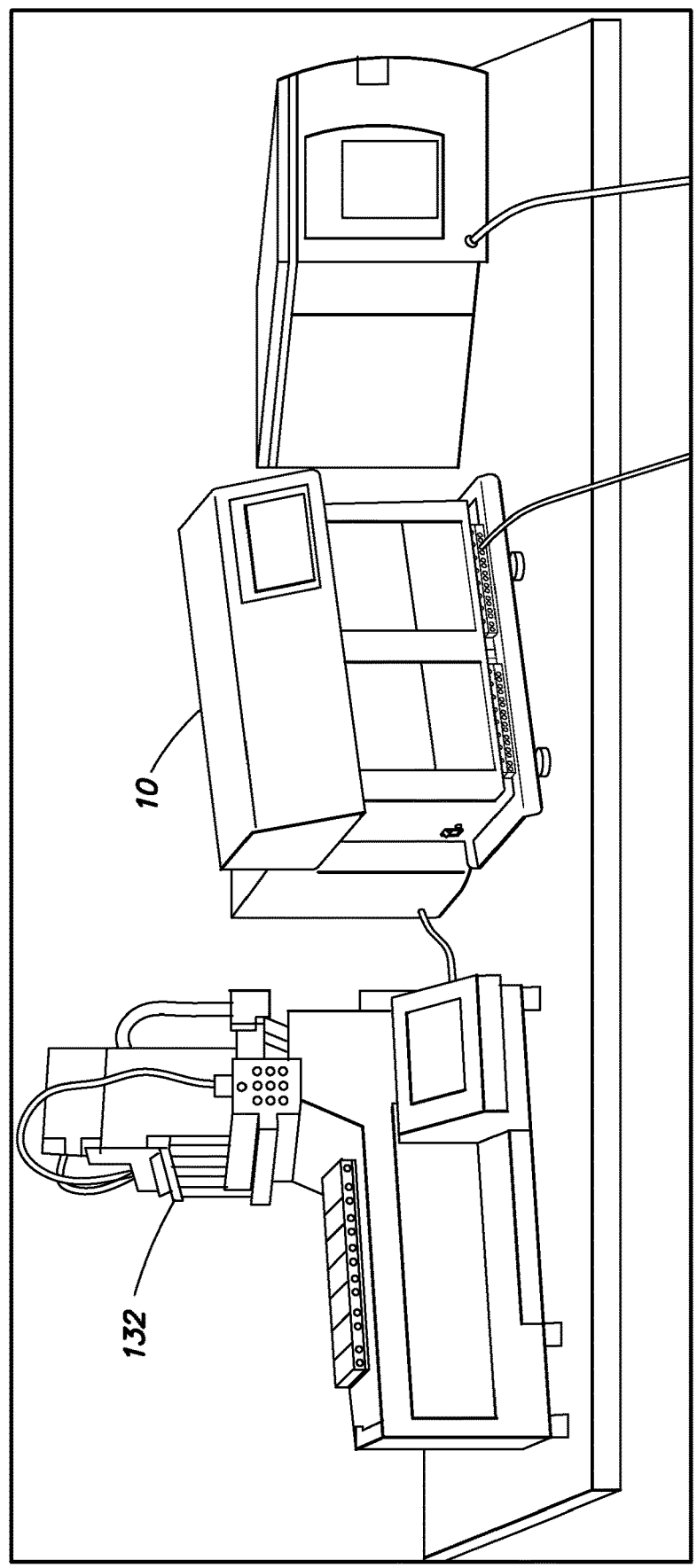
FIG. 10 is a schematic of the apparatus of FIG. 1 with a USP apparatus 3 release tester.

FIG. 10 is an arrangement in which the apparatus 10 is used with USP apparatus 3 release testers (designated 130 of a type manufactured by Logan Instruments Corporation). An exemplifying schematic of this use of apparatus 10 is shown in FIG. 11. To operate with USP apparatus 3 release testers 130, an exemplifying method is as follows:

1. Six tablets, as an example of a pharmaceutical product for which permeation and dissolution information is sought, are placed into tubes of the USP apparatus 130 for dissolution.

2. After dissolution is completed, six samples are taken for dissolution and permeation studies.

3. Syringe or other pumps from dissolution sampling pump arrangement 22 of apparatus 10 take six dissolution samples collected into glass tubes or other vessels, e.g., retained on the apparatus 10 or elsewhere, at the sample interval and then transfer the dissolution samples from six of the USP apparatus 3 tubes to the donor cell for permeation tests.

4. Over time, the dissolution sample in each donor cell slowly penetrates the membrane 66 of the respective permeation testing cell unit 14 (representing for example an intestinal wall) and then is transferred into the media in the chamber 46 of the receptor cells (the intestinal fluid or other bodily fluid).

5. Syringe pumps of permeation sampling pump arrangement 24 are actuated to take the pre-heated media from the respective vessel contained in the water bath 26. This actuation may occur simultaneous with or after the actuation of the syringe or other pumps of dissolution sampling pump arrangement 22.

6. Syringe or other pumps of dissolution sampling pump arrangement 22 are continually transferring the dissolution samples from the six channels into the donor cells through donor inlet component 72 and donor outlet component 78 which are looped with the dissolution sampling pump arrangement 22 and the interior of the vessels.

7. Permeation sampling pump arrangement 24 is actuated periodically to take permeation samples and collect them into tubes, retained by the apparatus or elsewhere. It is often desired to wait a set period of time until media from chamber 46 is removed from the receptor housing 42, e.g., two hours. Thus, a timing mechanism is provided to time the process and refrain from removing bodily fluid from the chamber 46 through the receptor inlet/outlet connector 38 until the set period of time has elapsed.

Often, this process takes hours and up to twenty sets, dissolution and permeation samples can be taken. It is then possible to analyze the samples and obtain the dissolution rate and the permeation rate, or other dissolution and/or permeation information as known to those skilled in the art to which this invention pertains. In combination with dissolution testing, apparatus 10 therefore simplifies and automates the process by means of which samples of bodily fluid into which pharmaceutical products have been transferred after passing through the membrane 66 are obtained and prepared for analysis to determine permeation rate of the pharmaceutical product into the bodily fluid through the membrane 66.

Figure 11:
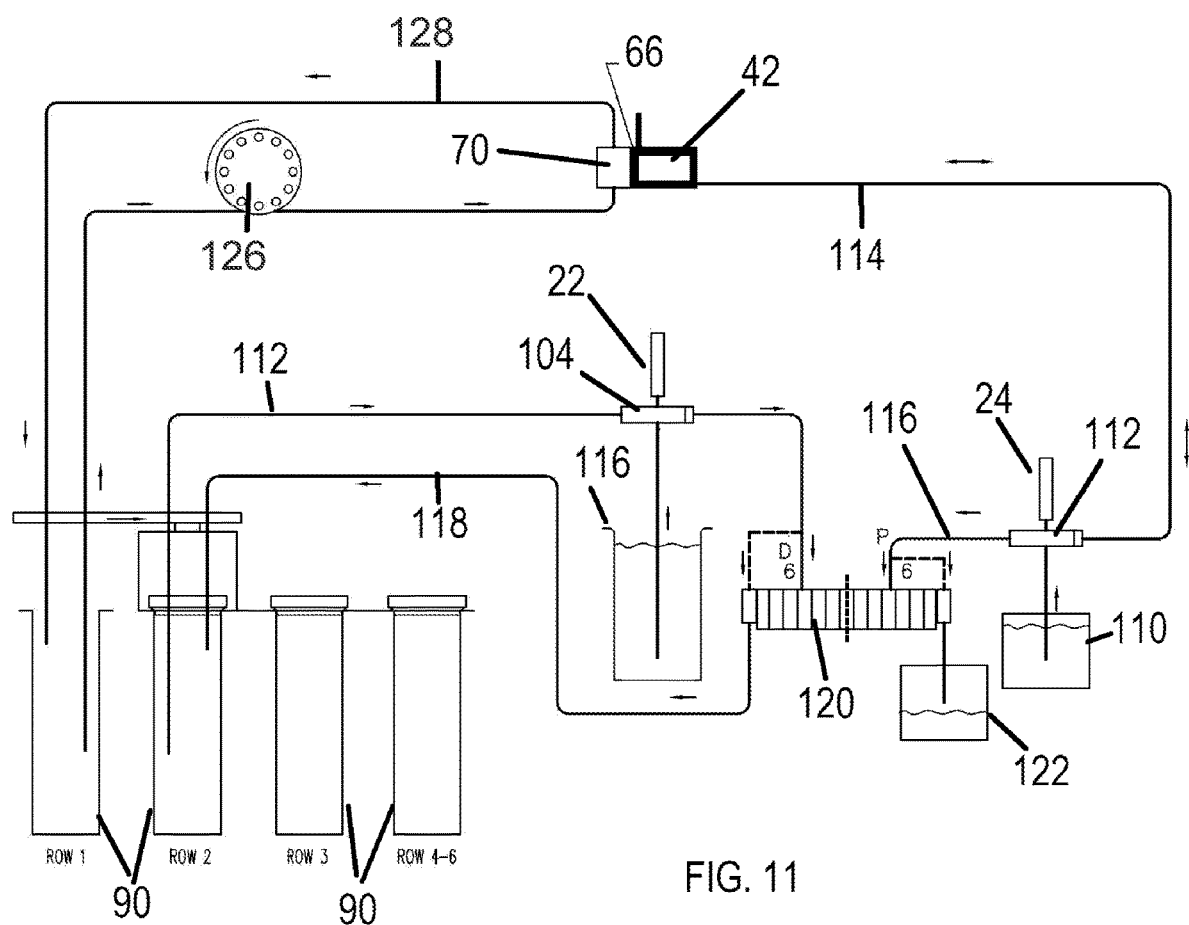
FIG. 11 is a flow schematic of one manner of use of the arrangement of FIG. 10.

FIG. 11 is a schematic of the one manner in which permeation testing can be achieved using the arrangement in accordance with the invention (described above with respect to FIG. 10). The flow valves 104 of dissolution sampling pump arrangement 22 transfer dissolution samples from dissolution vessels 100 while the pharmaceutical tablets are dissolving using conduit system 102 and direct samples to the sample collector 120. Through a conduit system 108, the dissolution media is withdrawn from the chambers in the donor housing part 70 back to the respective one of the vessels 100. The peristaltic pump 126 or similar device transfers the dissolution samples from vessels 100 to the donor side of the permeation testing cell units 14 while the tablets are dissolving via the conduit system 128 including portions before and after the permeation testing cell units 14 in the flow direction. On the receptor side of the permeation testing cell unit 14, the permeation sampling pump arrangement 24 and flow valve(s) 112 thereof control the flow of the bodily fluid from the source of bodily fluid 110 and to and from the chambers 46 in a plurality of the receptor housings 42 (to the right of the membrane 66 in FIG. 9) through the conduit system 114. The permeation sampling pump arrangement 24 and flow valve(s) 112 thereof also direct, when desired or according to a program, bodily fluid from the chambers 46 through the conduit system 116 to the sample collector 120 to thereby deposit the bodily fluid in a plurality of sample-receiving vessels. As such, samples for both permeation testing and dissolution testing are obtained by the sample collector 120. Waste collector 122 receives the analyzed bodily fluid samples from the sample collector 120. Each conduit system may include one or more conduits and associated flow structure to provide for secure flow of the fluid between the connected components.

The methods programmed into the analysis unit or electronics 30 may be configured to control the entire dissolution testing process and the permeation testing process. One exemplifying control method could be designed to control the temperature of the water bath 26, control the temperature of the heater block 36, control the speed at which the mixing devices 60 operate (e.g., control the mixing control unit 30), control the dissolution sampling pump arrangement 22 to perform the circulation of the dissolution media and the sampling for dissolution rate testing, and control the permeation sampling pump arrangement 24 for effecting flow of bodily fluid into and out of the receptor cell and sampling the bodily fluid into which the pharmaceutical component permeated through the membrane. The analysis unit or electronics 30 would also control the sample collector and analyzer to obtain the desired information about dissolution and permeation. The mixing devices, e.g., an assembly of magnet stirrer 86, magnet stir bar 88, electric motor 90, pulley 92, pulley shaft 94 (see FIG. 5) may be controlled to operate at a speed anywhere between about 100 rpm and about 1000 rpm.

There are several advantages of the present invention that are manifested by the apparatus and methods disclosed above. For example, a major advantage of some embodiments of the present invention described above and otherwise disclosed herein is that when a dissolution system is linked with the permeation testing apparatus in accordance with the invention, pharmaceutical scientists can get a dissolution dissolving percentage report as well as a permeation rate analysis within hours. This expedited combined dissolution/permeation report enables adjustment of testing parameters for subsequent testing at a much quicker pace.

Another advantage of some embodiments is that the permeation testing apparatus and method disclosed above seamlessly work with any USP apparatus 1, apparatus 2 (8 or 12 position) 98, 124 or apparatus 3 system 130 which, provides dissolution and permeation data at the same time.

The illustrated embodiments and schematics generally show only a portion of the entire apparatus 10. Remaining portions of the apparatus and duplicates of the disclosed and illustrated portions. For example, there is no limitation on the number of vessels for which dissolution testing and permeation testing may be performed. The apparatus can include stricture for receiving only a single vessel for permeation testing, or only a single vessel for dissolution testing and a single vessel for permeation testing, or the same number of vessels for dissolution testing as for permeation testing. The same structure that is disclosed for performing dissolution testing would be duplicated when there are multiple dissolution testing stations, and the same structure that is disclosed for performing permeation testing would be duplicated when there are multiple dissolution testing stations. However, when common equipment may be used for multiple dissolution and/or permeation testing stations, it is preferable to use the common equipment. For example, the water bath 26 may be designed to receive multiple vessels, the vessel plate 34 designed to accommodate multiple vessels, and the control unit 30 configured to control multiple testing stations. One skilled in the art would readily understand which structure must be individual or independent for each testing stations and which structure can be used for multiple testing stations.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention. All of the prior art identified above is incorporated by reference herein.

The invention claimed is:

1. A testing apparatus for analyzing at least one property of a pharmaceutical product, comprising:
a housing having a frame;
temperature-controllable testing cell units on said frame, each of said testing cell units including a first donor chamber configured to receive dissolution media, first connecting means for enabling fluid flow into and out of said first donor chamber, a second receptor chamber configured to receive bodily fluid, second connecting means for enabling fluid flow into and out of said second receptor chamber, membrane retaining means for retaining a membrane between said first donor chamber and said second receptor chamber, and controllable mixing means for mixing the fluid flowing into and out of said second receptor chamber;
a first flow control arrangement coupled to said first connecting means and configured to operatively circulate dissolution media into and out of said first donor chamber, the dissolution media being formed upon dissolution of the pharmaceutical product;
a second flow control arrangement coupled to said second connecting means and configured to operatively circulate bodily fluid into and out of said second receptor chamber; and
an analysis unit configured to analyze bodily fluid removed from said second receptor chamber by said second flow control arrangement to provide data about permeation of the pharmaceutical product through the membrane into the bodily fluid.

2. The testing apparatus of claim 1, wherein said first flow control arrangement is configured to direct dissolution media removed from said first donor chamber to a sample collector and said second flow control arrangement is configured to direct bodily fluid removed from said second receptor chamber to said sample collector, said analysis unit being further configured to analyze the dissolution media removed from said first donor chamber by said first flow control arrangement and bodily fluid removed from said second receptor chamber by said second flow control arrangement to provide data about dissolution of the pharmaceutical product dissolved in the dissolution media and permeation of the pharmaceutical product through the membrane into the bodily fluid.

3. The testing apparatus of claim 1, wherein each of said temperature-controllable testing cell units comprises a first housing part defining said first donor chamber and a second housing part defining said second receptor chamber, further comprising clamping means for clamping said first and second housing parts together.

4. The testing apparatus of claim 1, further comprising a temperature control unit on said frame and configured to control temperature of said temperature-controllable testing cell units.

5. The testing apparatus of claim 1, further comprising a mixing control unit on said frame and configured to control actuation of said controllable mixing means to mix the fluid flowing into and out of said second receptor chamber.

6. The testing apparatus of claim 1, wherein said first flow control arrangement comprises a plurality of syringe pumps and said second flow control arrangement comprises a plurality of syringe pumps.

7. The testing apparatus of claim 1, further comprising a water bath configured to pre-heat the dissolution media to a user-selected temperature.

8. The testing apparatus of claim 1, wherein said membrane retaining means comprise a first annular gasket and a second annular gasket, said first and second annular gaskets being configured to be pressed toward one another.

9. The testing apparatus of claim 1, wherein each of said temperature-controllable testing cell units further comprises the membrane.

10. The testing apparatus of claim 1, further comprising a plurality of clamps, each of said plurality of clamps being configured to engage with a respective one of said temperature-controllable testing cell units and clamp two parts of the respective one of said temperature-controllable testing cell units together.

11. The testing apparatus of claim 1, wherein each of said temperature-controllable testing cell units includes a donor cell defining said first donor chamber and a receptor cell defining said second receptor chamber.

12. The testing apparatus of claim 11, further comprising a plurality of clamps, each of said plurality of clamps clamping said donor cell of a respective one of said temperature-controllable testing cell units against said receptor cell of the respective one of said temperature-controllable testing cell units.

13. The testing apparatus of claim 1, further comprising a display and control screen on said housing and coupled to said analysis unit.

14. The testing apparatus of claim 1, wherein said second connecting means comprise a receptor inlet/outlet component including a housing defining a flow passage therethrough for flow of the bodily fluid.

15. The testing apparatus of claim 1, wherein each of said temperature-controllable testing cell units comprises a receptor housing defining said second receptor chamber.

16. The testing apparatus of claim 15, wherein said receptor housing includes a circumferential wall having an opening leading to a channel extending to said second receptor chamber, said controllable mixing means being situated in said channel.

17. The testing apparatus of claim 16, further comprising a vent plug configured to vent air from said second receptor chamber.

18. The testing apparatus of claim 1, wherein each of said temperature-controllable testing cell units comprises a donor housing defining said first donor chamber.

19. The testing apparatus of claim 18, wherein said donor housing has a cylindrical portion.

20. The testing apparatus of claim 18, wherein said donor housing has a first opening leading to a channel extending to said first donor chamber and a second opening leading to a channel extending to said first donor chamber, each of said temperature-controllable testing cell units further comprising a donor inlet component connected to said first opening and a donor outlet component connected to said second opening, said first flow control arrangement being configured to direct dissolution media into said first donor chamber through said donor inlet component and out of said first donor chamber through said donor outlet component.

* * * * *